(12) United States Patent
Swett et al.

(10) Patent No.: US 8,597,618 B1
(45) Date of Patent: Dec. 3, 2013

(54) DENTIFRICE COMPOSITION

(71) Applicant: Toms's of Maine, Inc., Kennebunk, ME (US)

(72) Inventors: Tammy Swett, Raymond, ME (US); Julie Venell, Acton, ME (US); Chantal Bergeron, Kennebunkport, ME (US); Mark Dobrovolny, Scarborough, ME (US); Stefan Gafner, Kennebunkport, ME (US)

(73) Assignee: Tom's of Maine, Inc., Kennebunk, ME (US)

( * ) Notice: Subject to any disclaimer, the term of this patent is extended or adjusted under 35 U.S.C. 154(b) by 0 days.

(21) Appl. No.: 13/706,582

(22) Filed: Dec. 6, 2012

(51) Int. Cl.
*A61K 8/60* (2006.01)
*A61K 8/37* (2006.01)
*A61Q 11/00* (2006.01)

(52) U.S. Cl.
USPC .............................. 424/49; 424/54

(58) Field of Classification Search
None
See application file for complete search history.

(56) References Cited

U.S. PATENT DOCUMENTS

| | | | |
|---|---|---|---|
| 2,900,391 A | 8/1959 | Norman | |
| 4,720,573 A | 1/1988 | Lin | |
| 4,748,158 A | 5/1988 | Biermann et al. | |
| 2005/0244346 A1 | 11/2005 | Nakao et al. | |
| 2008/0171000 A1* | 7/2008 | Engelman et al. | 424/50 |
| 2008/0274062 A1* | 11/2008 | Bergeron et al. | 424/49 |
| 2010/0303737 A1* | 12/2010 | Hurtig | 424/48 |
| 2012/0201764 A1* | 8/2012 | Day et al. | 424/54 |

FOREIGN PATENT DOCUMENTS

WO    WO 97/25966    7/1997

OTHER PUBLICATIONS

"Final Report on the Safety Assessment of Sodium Lauryl Sulfate and Ammonium Lauryl Sulfate," Intl, J. Toxicol, J. Amer. Coll, Toxicol.), 1983 2(7):127-181.
Agner, 1991, "Susceptibility of Atopic Dermatitis Patients to Irritant Dermatitis Caused by Sodium Lauryl Sulphate," Acta Derm. Venereol. 71(4):296-300.
Brand et al., 1998, "Allergic Contact Dermatitis to Cocamidopropylbetaine in Hair Shampoo," Australas J. Dermatol. 39(2):121-122.
Carlsson et al., 2006, "Are pharmaceuticals potent environmental pollutants? Part II: Environmental risk assessments of selected pharmaceutical excipients," Science of the Total Environment, pp. 88-95.
Chahine et al., 1997, "The Effect of Sodium Lauryl Sulfate on Recurrent Aphthous Ulcers: A Clinical Study," Compend. Contin, Educ, Dent. 18(12);1238-1240.
De Groot et al., 1995, "Contact Allergy to Cocamidopropyl Betaine," Contact Dermatitis 33(6):419-422.
Foti et al., 2003, "The Role of 3-Dimethylaminopropylamine and Amidoamine in Contact Allergy to Cocamidoporpylbetaine," Contact Dermatitis 48(4):194-198.
Fowler et al,, 1997, "Allergy to Cocamidopropyl Betaine May Be Due to Amidoamine: A Patch Test and Product Use Test Study," Contact Dermatitis 37(6):276-281.
Fowler et al., 2004, "Allergy to Cocamidopropyl Betaine and Amidoamine in North America," Dermatitis 15(1):5-6.
Healy et al., 1999, "The Effect of a Sodium Lauryl Sulfate-Free Dentifrice on Patients with Recurrent Oral Ulceration," Oral Dis, 5(1);39-43.
Herlofson et al., 1994, "Sodium Lauryl Sulfate and Recurrent Aphthous Ulcers: A Preliminary Study," Acta. Odontol. Scand, 52(5):257-259.
Herlofson et al., 1996, "The Effect of Two Toothpaste Detergents on the Frequency of Recurrent Aphthous Ulcers," Acta Odontol. Scand. 54(3):150-153.
Korting et al., 1992, "Allergic Contact Dermatitis to Cocamidopropyl Betaine in Shampoo," J. Amer. Acad. Dermatol. 27(6 pt. 1):1013-1015.
Loffler et al., 1999, "Skin Susceptibility of Atopic Individuals," Contact Derm. 40(5):239-242.
Marrakchi et al,, 2006, "Sodium Lauryl Sulfate-Induced Irritation in the Human Face: Regional and Age-Related Differences," Skin Pharmacol. Physiol. 19(3):177-180.
Mowad, 2001, "Cocamidopropyl Betaine Allergy," Amer. J. Contact Dermat. 12(4):223-224.
Nassif et al,, 1994, "Abnormal Skin Irritancy in Atopic Dermatitis and and in Atopy without Dermatitis," Arch. Dermatol. 130(11):1402-1407.
Piret et al., 2000, "In vitro and in vivo Evaluations of Sodium Lauryl Sulfate and Dextran Sulfate as Microbicides against Herpes Simplex and Human Immunodeficiency Viruses," J. Clin. Microbiol. 38(1):110-119.
Piret et al., 2002, "Sodium Lauryl Sulfate, a Microbicide Effective against Enveloped and Nonenveloped Viruses," Curr. Drug Targets 3(1):17-30.
Shaffer et al., 2006 "Allergenicity and Cross-Reactivity of Coconut Oil Derivatives: A Double-Blind Randomized Controlled Pilot Study," Dermatitis 17(2):71-76.
Tom's of Maine, 2012, website listing Sodium Cocyl Glutamate as a Surfactant, http://www.tomsofmaine.com/research/ingredients/ingredient-detail/sodium-cocoyl-gluta . . . .

* cited by examiner

*Primary Examiner* — Frederick Krass
*Assistant Examiner* — Celeste A Roney
(74) *Attorney, Agent, or Firm* — Howard C. Lee

(57) ABSTRACT

Disclosed is a dentifrice composition comprising an orally acceptable vehicle, an abrasive particulate and a surfactant system comprising an anionic surfactant comprising a C8-C16 fatty acid glutamate salt and a nonionic surfactant comprising a C8-C16 alkyl glucoside.

21 Claims, No Drawings

DENTIFRICE COMPOSITION

BACKGROUND OF THE INVENTION

Known dentifrice compositions, for example toothpastes or gels, have a variety of different formulations. When the dentifrice composition is formulated to generate foam in the mouth, such as when brushing the teeth, a surfactant is present to generate the foam. A widely used surfactant in dentifrice formulations is sodium lauryl sulfate (SLS), an anionic surfactant. Sodium lauryl sulfate is used in most commercially available toothpastes.

Sodium lauryl sulfate generates a widely recognised foam profile during brushing. Furthermore, sodium lauryl sulfate does not negatively impact the flavor profile of the dentifrice formulation or significantly affect the flavor of added flavorants. In other words, consumers who have wide experience of different commercially available dentifrice formulations have an expectation of foam profile and flavor which is, even if latently, associated by the consumer with the use of sodium lauryl sulfate in commercially available toothpastes.

Consumer studies show that there is a desire by some consumers to use a dentifrice which does not contain any sodium lauryl sulfate. One reason for this desire is that some consumers are sensitive to this ingredient. However, such consumers may nevertheless expect the dentifrice to have familiar foaming, flavor and texture properties.

Accordingly, there exists a need in the art for a dentifrice composition which can provide a consumer-desired foaming and flavor profile yet does not necessarily contain any sodium lauryl sulfate.

There also exists a need in the art for a surfactant system in a dentifrice composition which can provide a foaming and flavor profile similar to that provided by sodium lauryl sulfate so that the surfactant system may be employed as an effective replacement for sodium lauryl sulfate surfactant in dentifrice compositions.

BRIEF SUMMARY OF THE INVENTION

The present invention aims at least partially to meet either or both of these needs in the art.

The present invention accordingly provides a dentifrice composition comprising an orally acceptable vehicle, an abrasive particulate and a surfactant system comprising an anionic surfactant comprising a C8-C16 fatty acid glutamate salt and a nonionic surfactant comprising a C8-C16 alkyl glucoside.

Optionally, the C8-C16 fatty acid glutamate salt comprises a cocoyl glutamate salt.

Typically, the C8-C16 fatty acid glutamate salt comprises sodium cocoyl glutamate.

Optionally, the C8-C16 fatty acid glutamate salt is present in an amount of from 0.25 to 1.5 wt % based on the weight of the dentifrice composition, further optionally from 0.5 to 1.0 wt % based on the weight of the dentifrice composition, still further optionally from 0.65 to 0.85 wt % based on the weight of the dentifrice composition.

Typically, the C8-C16 fatty acid glutamate salt is present in an amount of 0.75 wt % based on the weight of the dentifrice composition.

Optionally, the C8-C16 alkyl glucoside comprises a C10-C14 alkyl glucoside.

Further optionally, the C10-C14 alkyl glucoside comprises lauryl glucoside.

Optionally, the C8-C16 alkyl glucoside is present in an amount of from 0.25 to 1.5 wt % based on the weight of the dentifrice composition, further optionally from 0.5 to 1.0 wt % based on the weight of the dentifrice composition, still further optionally from 0.65 to 0.85 wt % based on the weight of the dentifrice composition.

Typically, the C8-C16 alkyl glucoside is present in an amount of 0.75 wt % based on the weight of the dentifrice composition.

Optionally, the abrasive particulate comprises silica.

Optionally, the abrasive particulate is present in an amount of from 15 to 35 wt % based on the weight of the dentifrice composition, further optionally from 20 to 30 wt % based on the weight of the dentifrice composition.

Optionally, the orally acceptable vehicle comprises at least one humectant which is present in an amount of from 35 to 75 wt % based on the weight of the dentifrice composition, further optionally from 45 to 65 wt % based on the weight of the dentifrice composition.

Optionally, the at least one humectant comprises a mixture of sorbitol, glycerin and xylitol. Typically, the orally acceptable vehicle comprises from 25 to 45 wt % sorbitol, from 5 to 15 wt % glycerin and from 5 to 15 wt % xylitol, each amount being based on the weight of the dentifrice composition.

Optionally, the dentifrice composition further comprises at least one flavorant selected from spearmint and peppermint or a combination thereof, the flavorant being present in an amount of from 0.5 to 1.5 wt % based on the weight of the dentifrice composition.

Optionally, the orally acceptable vehicle comprises at least one gum selected from carrageenan and xanthan gum. Further optionally, the orally acceptable vehicle comprises from 0.1 to 0.3 wt % carrageenan and from 0.25 to 0.65 wt % xanthan gum, each amount being based on the weight of the dentifrice composition.

Typically, the dentifrice composition does not comprise any fluoride compound or source of fluorine ions.

Typically, the dentifrice composition does not comprise any alkyl sulfate salt.

The present invention further provides the use, in a dentifrice composition comprising an orally acceptable vehicle and an abrasive particulate, which dentifrice composition does not comprise any alkyl sulfate salt, of a surfactant system comprising an anionic surfactant comprising a cocoyl glutamate salt in an amount of from 0.65 to 0.85 wt % based on the weight of the dentifrice composition and a nonionic surfactant comprising lauryl glucoside in an amount of from 0.65 to 0.85 wt % based on the weight of the dentifrice composition, for enhancing the foaming and flavor of the dentifrice composition when applied to the oral cavity in a method of brushing the teeth.

The invention is predicated on the finding by the present inventors that a mixed surfactant system, comprising an anionic surfactant comprising a C8-C16 fatty acid glutamate salt and a nonionic surfactant comprising a C8-C16 alkyl glucoside, in particular when used in particular amounts, can provide a dentifrice composition, in particular a toothpaste, which meets the foam, flavor and texture expectations of consumers so that the C8-C16 fatty acid glutamate salt/C8-C16 alkyl glucoside mixed surfactant system can be used as a replacement for sodium lauryl sulfate in dentifrice compositions.

DETAILED DESCRIPTION OF THE INVENTION

As used herein, "dentifrice" refers to a paste, gel, or liquid formulation. In some embodiments, the dentifrice is deep striped, surface striped, or multilayered.

The expressions "vehicle" or "aqueous vehicle" as used throughout this description denote any safe and effective materials for use herein. Such materials include, for example, thickening agents, humectants, ionic active ingredients, buffering agents, anticalculus agents, abrasive polishing materials, peroxide sources, alkali metal bicarbonate salts, titanium dioxide, coloring agents, flavor systems, sweetening agents, antimicrobial agents, herbal agents, desensitizing agents, stain reducing agents, and mixtures thereof.

Surfactants

Surfactants are used in the dentifrice composition of the present invention to provide foaming, taste, flavor, texture and mouthfeel properties to the dentifrice compositions, in particular to render the dentifrice compositions more cosmetically acceptable. In particular embodiments, the surfactants used in the dentifrice composition of the present invention are employed to provide such properties which are substantially cosmetically equivalent to dentifrice compositions incorporating sodium lauryl sulfate. The surfactant components are each a detersive material that imparts to the composition detersive and foaming properties.

The surfactant system comprises an anionic surfactant comprising a C8-C16 fatty acid glutamate salt and a nonionic surfactant comprising a C8-C16 alkyl glucoside.

In the preferred embodiments the C8-C16 fatty acid glutamate salt comprises a cocoyl glutamate salt, in particular sodium cocoyl glutamate.

In the preferred embodiments the C8-C16 fatty acid glutamate salt is present in an amount of from 0.25 to 1.5 wt % based on the weight of the dentifrice composition, further optionally from 0.5 to 1.0 wt % based on the weight of the dentifrice composition, still further optionally from 0.65 to 0.85 wt % based on the weight of the dentifrice. Typically, the C8-C16 fatty acid glutamate salt is present in an amount of 0.75 wt % based on the weight of the dentifrice composition.

In the preferred embodiments the C8-C16 alkyl glucoside comprises a C10-C14 alkyl glucoside, in particular lauryl glucoside.

In the preferred embodiments the C8-C16 alkyl glucoside is present in an amount of from 0.25 to 1.5 wt % based on the weight of the dentifrice composition, further optionally from 0.5 to 1.0 wt % based on the weight of the dentifrice composition, still further optionally from 0.65 to 0.85 wt % based on the weight of the dentifrice composition. Typically, the C8-C16 alkyl glucoside is present in an amount of 0.75 wt % based on the weight of the dentifrice composition.

Other surfactants, which may be anionic, cationic, zwitterionic, amphoteric or nonionic, and are known for use in dentifrice compositions, may optionally be present in the composition. However, preferably the dentifrice composition does not comprise any alkyl sulfate salt, in particular sodium lauryl sulfate.

Dentifrice Vehicle

Orally-acceptable vehicles used to prepare the dentifrice composition of the present invention may include a water-phase containing at least one humectant.

The humectant concentration typically totals 5 to 75% by weight of the dentifrice composition.

Optionally, the orally acceptable vehicle comprises at least one humectant which is present in an amount of from 35 to 75 wt % based on the weight of the dentifrice composition, further optionally from 45 to 65 wt % based on the weight of the dentifrice composition.

Optionally, the at least one humectant comprises a mixture of sorbitol, glycerin and xylitol. Typically, the orally acceptable vehicle comprises from 25 to 45 wt % sorbitol, from 5 to 15 wt % glycerin and from 5 to 15 wt % xylitol, each amount being based on the weight of the dentifrice composition. Reference herein to sorbitol refers to the material typically commercially available as a 70 wt % aqueous solution. In other words, when the orally acceptable vehicle comprises from 25 to 45 wt % sorbitol, this means the active sorbitol concentration is from 17.5 to 22.5 wt %, each amount being based on the weight of the dentifrice composition.

The humectant is preferably glycerin, sorbitol, xylitol, and/or propylene glycol of molecular weight in the range of 200 to 1,000; but, other humectants and mixtures thereof may also be employed.

Water is present typically in amount of at least 10 wt %, and generally 25 to 70 wt % of the dentifrice composition. Water employed in the preparation of commercially suitable oral compositions should preferably be deionized and free of organic impurities. These amounts of water include the free water which is added plus that which is introduced with other materials such as with sorbitol.

Abrasives

The dentifrice composition of the invention incorporates an abrasive particulate component.

Abrasives that may be used in preparing the dentifrice compositions include silica abrasives such as precipitated or hydrated silicas having a mean particle size of up to 20 microns. Other useful dentifrice abrasives include sodium metaphosphate, potassium metaphosphate, tricalcium phosphate, dihydrated dicalcium phosphate, aluminum silicate, calcined alumina, bentonite or other siliceous materials, or combinations thereof.

Preferred abrasive materials useful in the practice of the preparation of the dentifrice compositions in accordance with the present invention include silica gels and precipitated amorphous silica having an oil absorption value of less than 100 cc/100 g silica and preferably in the range of from 45 cc/100 g to less than 70 cc/100 g silica. These silicas are colloidal particles having an average particle size ranging from 3 microns to 12 microns, and more preferably between 5 to 10 microns and a pH range from 4 to 10 preferably 6 to 9 when measured as a 5% by weight slurry.

Optionally, the abrasive particulate is present in an amount of from 15 to 35 wt % based on the weight of the dentifrice composition, further optionally from 20 to 30 wt % based on the weight of the dentifrice composition.

The dentifrice composition of the invention can contain a variety of optional dentifrice ingredients. As described below, such optional ingredients can include, but are not limited to, thickening agents, antitartar agents, a source of fluoride ions, stabilizers, a synthetic anionic polycarboxylate, a flavoring agent, and coloring agents.

Thickening Agents

Thickeners suitable of use in the composition of the present invention include natural and synthetic gums and colloids. Optionally, the orally acceptable vehicle comprises at least one gum selected from carrageenan and xanthan gum. Further optionally, the orally acceptable vehicle comprises from 0.1 to 0.3 wt % carrageenan and from 0.25 to 0.65 wt % xanthan gum, each amount being based on the weight of the dentifrice composition.

Suitable thickeners include naturally occurring polymers such as carrageenan, xanthan gum, polyglycols of varying molecular weights sold under the tradename Polyox, and polyvinylpyrrolidone. Compatible inorganic thickeners include amorphous silica compounds which function as thickening agents and include colloidal silicas compounds available under the trade designation Cab-o-sil manufactured by Cabot Corporation and distributed by Lenape Chemical, Bound Brook, N.J.; Zeodent 165 from J. M. Huber Chemicals Division, Havre de Grace, Md. 21078; and Sylodent 15, available from Davison Chemical Division of W. R. Grace Corporation, Baltimore, Md. 21203. Other inorganic thickeners include natural and synthetic clays such as hectorite clays, lithium magnesium silicate (laponite) and magnesium aluminum silicate (Veegum).

The thickening agent preferably is present in the dentifrice composition in amounts of 0.1 to 10 wt %, preferably 3 to 7 wt % based on the weight of the dentifrice composition.

Fluoride and Other Active Agents

The dentifrice composition of the present invention may also contain a source of fluoride ions or fluorine-providing component, as anticaries agent in amount sufficient to supply 25 ppm to 5,000 ppm of fluoride ions and include inorganic fluoride salts, such as soluble alkali metal salts. For example, preferred fluoride sources are sodium fluoride, potassium fluoride, sodium fluorosilicate, ammonium fluorosilicate, as well as tin fluorides, such as stannous fluoride and stannous chloride. Sodium fluoride is preferred.

However, in some preferred embodiments, the dentifrice does not comprise any fluoride compound or source of fluorine ions. Such embodiments are desired by some consumers who wish to avoid fluorine as an active component in their dentifrice composition.

In addition to fluoride compounds, there may also be included antitartar agents such as pyrophosphate salts including dialkali or tetraalkali metal pyrophosphate salts such as $Na_4P_2O_7$, $K_4P_2O_7$, $Na_2K_2P_2O_7$, $Na_2H_2P_2O_7$ and $K_2H_2P_2O_7$ sodium tripolyphosphate, long chain polyphosphates such as sodium hexametaphosphate and cyclic phosphates such as sodium trimetaphosphate. These antitartar agents may be included in the dentifrice composition at a concentration of 1 to 5 wt %.

Anionic Polycarboxylate

Synthetic anionic polycarboxylates may also be used in the dentifrice compositions of the present invention as an efficacy enhancing agent for any antibacterial, antitartar or other active agent within the dentifrice composition. Such anionic polycarboxylates are generally employed in the form of their free acids or preferably partially or more preferably fully neutralized water-soluble alkali metal (e.g. potassium and preferably sodium) or ammonium salts. Preferred are 1:4 to 4:1 copolymers of maleic anhydride or acid with another polymerizable ethylenically unsaturated monomer, preferably methylvinylether/maleic anhydride having a molecular weight (M.W.) of 30,000 to 1,800,000 most preferably 30,000 to 700,000. Examples of these copolymers are available from GAF Corporation under the tradename Gantrez®, e.g. AN 139 (M.W. 500,000), AN 119 (M.W. 250,000); S-97 Pharmaceutical Grade (M.W. 700,000), AN 169 (M.W. 1,200,000-1,800,000), and AN 179 (M.W. above 1,800,000); wherein the preferred copolymer is S-97 Pharmaceutical Grade (M.W. 700,000).

When present, anionic polycarboxylates can be employed in amounts effective to achieve the desired enhancement of the efficacy of any antibacterial, antitartar or other active agent within the dentifrice composition. Generally, the anionic polycarboxylates are present within the dentifrice composition from 0.05 wt % to 4 wt %, typically from 0.5 wt % to 2.5 wt %.

Flavor

The dentifrice composition of the present invention may also contain a flavoring agent. Flavoring agents that are used in the practice of the present invention include essential oils as well as various flavoring aldehydes, esters, alcohols, and similar materials. Examples of the essential oils include oils of spearmint, peppermint, wintergreen, sassafras, clove, sage, eucalyptus, marjoram, cinnamon, lemon, lime, grapefruit, and orange. Also useful are such chemicals as menthol, carvone, and anethole. Of these, the most commonly employed are the oils of peppermint and spearmint.

The flavoring agent may be incorporated in the dentifrice composition at a concentration of 0.1 to 5 wt % and typically 0.5 to 1.5 wt %.

Optionally, the dentifrice further comprises at least one flavorant selected from spearmint and peppermint or a combination thereof, the flavorant being present in an amount of from 0.5 to 1.5 wt % based on the weight of the dentifrice composition.

Other Ingredients

Various other materials may be incorporated in the dentifrice compositions of this invention, including desensitizers, such as potassium nitrate; whitening agents; preservatives; silicones; coloring agents; and chlorophyll compounds. These additives, when present, are incorporated in the dentifrice composition in amounts that do not substantially adversely affect the properties and characteristics desired.

Antibacterial agents may be incorporated in the dentifrice compositions of the invention. Common antibacterial agents used in oral care include triclosan, chlorohexidine, cetyl pyridinium chloride, and other quaternary amines. These agents, when present, are incorporated in the dentifrice composition in effective amounts that do not substantially adversely affect the desired properties and characteristics of the composition.

Preparation of Dentifrice Compositions

To prepare a dentifrice composition of the invention, generally the humectants such as glycerin, sorbitol and xylitol are dispersed in the water in a conventional mixer under agitation. Into the dispersion are added organic thickeners, such as xanthan gum and carrageenan; and any sweetener. The resultant mixture is agitated until a homogeneous gel phase is formed. Into the gel phase are added a colorant such as $TiO_2$, and any acid or base required to adjust the pH in the range of 6.4 to 7.3. These ingredients are mixed until a homogenous phase is obtained. The resultant mixture is then transferred to a high speed/vacuum mixer; wherein, the thickener, flavor components and surfactant ingredients are added to the mixture. Thereafter the abrasive is added. The mixture is then mixed at high speed for a typical period of from 5 to 30 minutes, typically under vacuum of from 20 to 50 mm of Hg, preferably 30 mm Hg. The resultant product is a homogeneous, semi-solid, extrudable paste or gel product.

Various embodiments now will be described with reference to the following non-limiting examples

EXAMPLES

Examples 1 to 5

Dentifrice compositions having the formulae of Examples 1 to 5 specified in Table 1 were prepared. Examples 1 to 5 are embodiments of the invention.

These dentifrice compositions included, as a surfactant system, a mixture of sodium cocoyl glutamate added as a 30 wt % aqueous solution and lauryl glucoside added as a 30 wt % aqueous solution. Examples 1 to 5 differed in their flavor and mouthfeel components, Examples 1 and 2 incorporating aloe, chamomile and spearmint and Examples 3 to 5 incorporating propolis and peppermint.

Examples 1 and 3 included 2.50 wt % sodium cocoyl glutamate added as a 30 wt % aqueous solution and therefore providing 0.75 wt % active surfactant in the total composition and 2.50 wt % lauryl glucoside added as a 30 wt % aqueous solution and therefore providing 0.75 wt % active surfactant in the total composition. Examples 2 and 4 included 2.00 wt % sodium cocoyl glutamate added as a 30 wt % aqueous solution and therefore providing 0.60 wt % active surfactant in the total composition and 2.00 wt % lauryl glucoside added as a 30 wt % aqueous solution and therefore providing 0.60 wt % active surfactant in the total composition. Example 5 included 3.00 wt % sodium cocoyl glutamate added as a 30 wt % aqueous solution and therefore providing 0.90 wt % active surfactant in the total composition and 3.00 wt % lauryl glucoside added as a 30 wt % aqueous solution and therefore providing 0.90 wt % active surfactant in the total composition. Sorbitol was added as a 70 wt % aqueous solution.

TABLE 1

Dentifrice Compositions

| Ingredient | Ex. 1 | Ex. 2 | Ex. 3 | Ex. 4 | Ex. 5 |
|---|---|---|---|---|---|
| Glycerin | 10.0 | 10.0 | 10.0 | 10.0 | 10.0 |
| Carrageenan | 0.2 | 0.2 | 0.2 | 0.2 | 0.2 |
| Xanthan gum | 0.45 | 0.45 | 0.45 | 0.45 | 0.45 |
| Sorbitol (70 wt % aqueous solution) | 35.755 | 35.755 | 36.014 | 36.014 | 36.014 |
| Xylitol | 10.0 | 10.0 | 10.0 | 10.0 | 10.0 |
| Zeodent 114 silica | 10.0 | 10.0 | 10.0 | 10.0 | 10.0 |
| Zeodent 105 silica | 10.0 | 10.0 | 10.0 | 10.0 | 10.0 |
| Zeodent 165 silica | 5.0 | 5.0 | 5.0 | 5.0 | 5.0 |
| Titanium dioxide | 0.25 | 0.25 | 0.25 | 0.25 | 0.25 |
| Lauryl glucoside (30 wt % aqueous solution) | 2.50 | 2.00 | 2.50 | 2.00 | 3.00 |
| Sodium cocoyl glutamate (30 wt % aqueous solution) | 2.50 | 2.00 | 2.50 | 2.00 | 3.00 |
| Aloe | 0.04 | 0.04 | — | — | — |
| Chamomile extract | 0.025 | 0.025 | — | — | — |
| Spearmint flavor | 1.0 | 1.0 | — | — | — |
| Propolis | — | — | 0.006 | 0.006 | 0.006 |
| Peppermint flavor | — | — | 0.80 | 0.80 | 0.80 |
| Sweetener | 0.08 | 0.08 | 0.08 | 0.08 | 0.08 |
| Water | Balance to 100% | Balance to 100% | Balance to 100% | Balance to 100% | Balance to 100% |

To evaluate the flavor of the dentifrice formulae, the dentifrice compositions were subjected to a statistically robust consumer test. The flavor of the dentifrice was tested by consumers both after initial manufacture of the dentifrice compositions and after a 6 week aging period.

The results are shown in Table 2.

TABLE 2

| Dentifrice Composition | Consumer Test Result-Initial | Consumer Test Result-After 6 weeks aging |
|---|---|---|
| Example 1 | Pass | Pass |
| Example 2 | Fail | Fail |
| Example 3 | Pass | Pass |
| Example 4 | Fail | Not Tested |
| Example 5 | Pass | Fail |

It may be seen that with these particular flavor and mouthfeel components, namely aloe, chamomile and spearmint or propolis and peppermint, the best flavor was found to be provided by the compositions of Examples 1 and 3 which each had 2 wt %, providing 0.75 wt % active surfactant component, of each of sodium cocoyl glutamate and lauryl glucoside.

However, other flavor and mouthfeel components may provide acceptable flavor of other dentifrice formulations containing the amounts of sodium cocoyl glutamate and lauryl glucoside of Examples 2, 4 and 5. As evidenced below, using 2 wt % (30% active) for each of the sodium cocoyl glutamate and lauryl glucoside surfactant components in a dentifrice composition was found to provide significantly lower potential irritancy as compared to sodium lauryl sulfate yet similar foam properties as compared to sodium lauryl sulfate.

To evaluate the potential irritancy of the dentifrice formulae, surfactant components were diluted in water and tested using an EpiOral in Vitro Irritation Test Method, in particular the EpiOral ORL-200 model, a known model for testing irritant potential of dentifrice components.

In the EpiOral test, the dentifrice components were tested to determine the parameter "ET-50" which represents the time at which 50% of cells are viable: the higher the ET-50 time then the less irritating the material. The termination time for the test was 240 minutes.

The results are shown in Table 3.

TABLE 3

| Dentifrice Component | Concentration in water wt % | ET-50 Time (minutes) |
|---|---|---|
| Sodium lauryl sulfate | 1 | 115.4 |
| Sodium lauryl sulfate | 2 | 48.3 |
| Lauryl glucoside | 1 | >240 |
| Lauryl glucoside | 2 | >240 |
| Sodium cocoyl glutamate | 1 | >240 |
| Sodium cocoyl glutamate | 2 | >240 |

It may be seen that sodium lauryl sulfate exhibited high potential irritancy whereas both lauryl glucoside and sodium cocoyl glutamate very low potential irritancy at different concentrations.

Dentifrice compositions incorporating different surfactant systems were also subjected to the EpiOral test.

The results are shown in Table 4.

TABLE 4

| Surfactant(s) in Dentifrice Composition | ET-50 Time (hours) |
|---|---|
| 5 wt % sodium lauryl sulfate | 2.0-2.3 |
| 2.25 wt % sodium lauryl sulfate | 13.5-14.9 |
| 3 wt % (30% active) lauryl glucoside and 3 wt % (30% active) sodium cocoyl glutamate | 13.5-14.9 |
| 2 wt % (30% active) lauryl glucoside and 2 wt % (30% active) sodium cocoyl glutamate | >18 |
| 2.5 wt % (30% active) lauryl glucoside and 2.5 wt % (30% active) sodium cocoyl glutamate | >18 |

It may be seen that the dentifrice compositions having 2 wt % (30% active) or 2.5 wt % (30% active) of each of lauryl glucoside and sodium cocoyl glutamate exhibited the lowest irritation potential.

A dentifrice composition incorporating 5 wt % sodium lauryl sulfate, and so not according to the invention, had an ET-50 of from 2.0 to 2.3 hours. A dentifrice composition incorporating 2.25 wt % sodium lauryl sulfate had an ET-50 of from 13.5 to 14.9 hours. A dentifrice composition according to an embodiment of the invention incorporating 3 wt % (30% active) lauryl glucoside and 3 wt % (30% active)

sodium cocoyl glutamate had an ET-50 of from 13.5 to 14.9 hours. A dentifrice composition according to an embodiment of the invention incorporating 2 wt % (30% active) lauryl glucoside and 2 wt % (30% active) sodium cocoyl glutamate had an ET-50 of greater than 18 hours. A dentifrice composition according to an embodiment of the invention incorporating 2 wt % (30% active) lauryl glucoside and 2 wt % (30% active) sodium cocoyl glutamate had an ET-50 of greater than 18 hours.

To evaluate the foaming efficacy of the dentifrice formulae, the dentifrice compositions were subjected to a foam evaluation. A common dose of each formulation was mixed with water and agitated.

The resultant foam was evaluated for the criteria of dispersability (a low score is slow, a high score is fast), foam thickness (a low score is thin, a high score is thick) and amount of foam (a low score is less, a high score is more).

The results are shown in Table 5.

TABLE 5

| Surfactant system in dentifrice | Dispersability | Foam thickness | Foam amount |
| --- | --- | --- | --- |
| 2 wt % (30% active) lauryl glucoside and 2 wt % (30% active) sodium cocoyl glutamate | 2.5 | 3.0 | 3.0 |
| 2.5 wt % (30% active) lauryl glucoside and 2.5 wt % (30% active) sodium cocoyl glutamate | 3.0 | 4.0 | 3.0 |
| 3.0 wt % (30% active) lauryl glucoside and 3.0 wt % (30% active) sodium cocoyl glutamate | 3.5 | 4.0 | 3.5-4.5 |
| 5 wt % sodium lauryl sulfate | 3.5 | 5.0 | 5.0 |
| 2.25 wt % sodium lauryl sulfate | 2.5 | 3.5 | 3.0 |

It may be seen that when the amount of each of lauryl glucoside and sodium cocoyl glutamate in the dentifrice is within the range of 2 wt % (30% active) to 3 wt % (30% active), the foam properties are similar to dentifrice formulations incorporating typically commercially used amounts of sodium lauryl sulfate. In other words, by providing these amounts of lauryl glucoside and sodium cocoyl glutamate as a combination surfactant system in the dentifrice composition, sodium lauryl sulfate can be omitted, and these combined surfactants can replace sodium lauryl sulfate without compromising foam quality as expected by a consumer familiar with typical commercial dentifrice compositions incorporating sodium lauryl sulfate.

Furthermore, each of the surfactant components, sodium lauryl sulfate, lauryl glucoside and sodium cocoyl glutamate, was individually tested for foaming capability when admixed with water and agitated. The foaming ability was determined by a numerical score, 1 representing an excellent foamer and 5 representing a poor foamer The results are shown in Table 6.

TABLE 6

| Surfactant | Foaming ability |
| --- | --- |
| Sodium lauryl sulfate | 1 |
| Sodium cocoyl glutamate | 5 |
| Lauryl glucoside | 3 |

It may be seen that with these particular surfactant components, each of lauryl glucoside and sodium cocoyl glutamate was found individually to have a significantly poorer foaming ability as compared to sodium lauryl sulfate.

However, as shown in Table 5, in a dentifrice composition the surfactant system of the combination of lauryl glucoside and sodium cocoyl glutamate was found to have a substantially similar foaming ability as compared to a dentifrice composition including sodium lauryl sulfate as the surfactant.

Consequently the surfactant system of the combination of lauryl glucoside and sodium cocoyl glutamate appears to provide enhanced foaming properties as compared to what would be expected from the performance of the individual components, and suggests an unexpected synergy between these two surfactant components which provides equivalent foaming to sodium lauryl sulfate when used in a dentifrice composition.

Accordingly, in summary the various experiments conducted by the inventors show cumulatively that the surfactant system of the combination of lauryl glucoside and sodium cocoyl glutamate can provide the combination of foaming properties, flavor and mouthfeel to enable this system to be formulated in a dentifrice composition as an effective consumer-acceptable replacement for sodium lauryl sulfate.

Various other modifications and embodiments of the dentifrice composition of the invention will be readily apparent to those skilled in the art.

The invention claimed is:

1. A dentifrice composition comprising
   an orally acceptable vehicle,
   an abrasive particulate and
   a surfactant system comprising an anionic surfactant comprising a C8-C16 fatty acid glutamate salt and a nonionic surfactant comprising a C8-C16 alkyl glucoside
   wherein the dentifrice does not comprise any fluoride compound or source of fluorine ions and does not comprise any alkyl sulfate salt.

2. The dentifrice composition according to claim 1 wherein the C8-C16 fatty acid glutamate salt comprises a cocoyl glutamate salt and the C8-C16 alkyl glucoside comprises a C10-C14 alkyl glucoside.

3. The dentifrice composition according to claim 2 wherein the C8-C16 fatty acid glutamate salt comprises sodium cocoyl glutamate and wherein the C10-C14 alkyl glucoside comprises lauryl glucoside.

4. The dentifrice composition according to claim 1 wherein the C8-C16 fatty acid glutamate salt is present in an amount of from 0.25 to 1.5 wt % based on the weight of the dentifrice composition and wherein the C8-C16 alkyl glucoside is present in an amount of from 0.25 to 1.5 wt % based on the weight of the dentifrice composition.

5. The dentifrice composition according to claim 4 wherein the C8-C16 fatty acid glutamate salt is present in an amount of from 0.5 to 1.0 wt % based on the weight of the dentifrice composition and wherein the C8-C16 alkyl glucoside is present in an amount of from 0.5 to 1.0 wt % based on the weight of the dentifrice composition.

6. The dentifrice composition according to claim 5 wherein the C8-C16 fatty acid glutamate salt is present in an amount of from 0.65 to 0.85 wt % based on the weight of the dentifrice composition and wherein the C8-C16 alkyl glucoside is present in an amount of from 0.65 to 0.85 wt % based on the weight of the dentifrice composition.

7. The dentifrice composition according to claim 2 wherein the abrasive particulate comprises silica.

8. The dentifrice composition according to claim 7 wherein the abrasive particulate is present in an amount of from 15 to 35 wt % based on the weight of the dentifrice composition and wherein the orally acceptable vehicle comprises at least one humectant which is present in an amount of from 35 to 75 wt % based on the weight of the dentifrice composition.

9. The dentifrice composition according to claim 8 wherein the abrasive particulate is present in an amount of from 20 to 30 wt % based on the weight of the dentifrice composition and wherein the at least one humectant is present in an amount of from 45 to 65 wt % based on the weight of the dentifrice composition.

10. The dentifrice composition according to claim 9 wherein the at least one humectant comprises a mixture of sorbitol, glycerin and xylitol.

11. The dentifrice composition according to claim 10 wherein the orally acceptable vehicle comprises from 25 to 45 wt % sorbitol, from 5 to 15 wt % glycerin and from 5 to 15 wt % xylitol, each amount being based on the weight of the dentifrice composition.

12. The dentifrice composition according to claim 1 further comprising at least one flavorant selected from spearmint and peppermint or a combination thereof, the flavorant being present in an amount of from 0.5 to 1.5 wt % based on the weight of the dentifrice composition.

13. The dentifrice composition according to claim 1 wherein the orally acceptable vehicle comprises at least one gum selected from carrageenan and xanthan gum.

14. The dentifrice composition according to claim 13 wherein the orally acceptable vehicle comprises from 0.1 to 0.3 wt % carrageenan and from 0.25 to 0.65 wt % xanthan gum, each amount being based on the weight of the dentifrice composition.

15. A method of enhancing the foaming and flavor of a first dentifrice composition when applied to the oral cavity in a method of brushing the teeth which comprises adding a foaming and flavor enhancing effective amount of the dentifrice composition of claim 1 to the first dentifrice composition.

16. The dentifrice composition according to claim 9 wherein the C8-C16 fatty acid glutamate salt is present in an amount of from 0.65 to 0.85 wt % based on the weight of the dentifrice composition and wherein the C8-C16 alkyl glucoside is present in an amount of from 0.65 to 0.85 wt % based on the weight of the dentifrice composition.

17. The dentifrice composition according to claim 16 wherein the C8-C16 fatty acid glutamate salt comprises sodium cocoyl glutamate and wherein the C10-C14 alkyl glucoside comprises lauryl glucoside.

18. The dentifrice composition according to claim 7 wherein the abrasive particulate is present in an amount of from 15 to 35 wt % based on the weight of the dentifrice composition and wherein the orally acceptable vehicle comprises at least one gum selected from carrageenan and xanthan gum.

19. The dentifrice composition according to claim 18 wherein the abrasive particulate is present in an amount of from 20 to 30 wt % based on the weight of the dentifrice composition and wherein the orally acceptable vehicle comprises from 0.1 to 0.3 wt % carrageenan and from 0.25 to 0.65 wt % xanthan gum, each amount being based on the weight of the dentifrice composition.

20. The dentifrice composition according to claim 19 wherein the C8-C16 fatty acid glutamate salt is present in an amount of from 0.65 to 0.85 wt % based on the weight of the dentifrice composition and wherein the C8-C16 alkyl glucoside is present in an amount of from 0.65 to 0.85 wt % based on the weight of the dentifrice composition.

21. The dentifrice composition according to claim 20 wherein the C8-C16 fatty acid glutamate salt comprises sodium cocoyl glutamate and wherein the C10-C14 alkyl glucoside comprises lauryl glucoside.

* * * * *